United States Patent

Hollands

Patent Number: 5,224,935
Date of Patent: Jul. 6, 1993

[54] CATHETER RETAINER

[75] Inventor: Keith G. M. Hollands, Sompting, England

[73] Assignee: E. R. Squibb & Sons, Inc., Princeton, N.J.

[21] Appl. No.: 975,209

[22] Filed: Nov. 12, 1992

Related U.S. Application Data

[63] Continuation of Ser. No. 690,475, Apr. 24, 1991, abandoned.

[30] Foreign Application Priority Data

May 2, 1990 [GB] United Kingdom ............... 9009840

[51] Int. Cl.⁵ .................................. A61M 5/32
[52] U.S. Cl. .......................... 604/180; 128/DIG. 26
[58] Field of Search ...................... 604/174–180, 604/264, 280; 128/DIG. 26

[56] References Cited

U.S. PATENT DOCUMENTS

| | | | |
|---|---|---|---|
| 2,669,231 | 2/1954 | Fisher | 604/179 |
| 3,568,679 | 3/1971 | Reif | 604/180 |
| 3,702,612 | 11/1972 | Schlesinger | 604/180 |
| 3,730,187 | 5/1973 | Reynolds | 604/179 X |
| 4,057,066 | 11/1977 | Taylor | 604/180 |
| 4,392,854 | 7/1983 | Ibach | 604/174 |
| 4,392,857 | 7/1983 | Beran | 604/179 |
| 4,419,094 | 12/1983 | Patel | 604/93 |
| 4,480,639 | 11/1984 | Peterson et al. | 128/207.18 |
| 4,498,903 | 2/1985 | Mathew | 604/174 |
| 4,579,120 | 4/1986 | MacGregor | 128/640 |
| 4,606,735 | 8/1986 | Wilder et al. | 604/180 |
| 4,650,473 | 3/1987 | Bartholomew et al. | 604/174 |
| 4,699,616 | 10/1987 | Nowak et al. | 604/180 |
| 4,795,442 | 1/1989 | Traflet | 604/179 |
| 4,820,282 | 4/1989 | Hogan | 604/263 |
| 4,857,058 | 8/1989 | Payton | 604/180 |
| 4,874,380 | 10/1989 | Hesketh | 604/180 |
| 4,906,233 | 3/1990 | Moriuchi et al. | 604/174 |

FOREIGN PATENT DOCUMENTS

| | | | |
|---|---|---|---|
| 0327299 | 8/1989 | European Pat. Off. | 604/180 |
| 2243554 | 11/1991 | United Kingdom | 604/180 |

OTHER PUBLICATIONS

"Silastic Cystocath Suprapubic Drainage System" Brochure, Dow Corning Bulletin 14-410, 6 pages, Aug. 1969.

*Primary Examiner*—John D. Yasko
*Assistant Examiner*—Adam J. Cermak
*Attorney, Agent, or Firm*—Stuart E. Krieger

[57] ABSTRACT

A catheter retainer is disclosed that includes an adhesive pad with projections. The catheter is secured to the pad by being tied to the projections.

4 Claims, 1 Drawing Sheet

CATHETER RETAINER

This is a continuation of application Ser. No. 07/690,475 filed Apr. 24, 1991, now abandoned.

BACKGROUND OF THE INVENTION

This invention relates to a catheter retainer.

Catheter retainers are well known. For example, one form of catheter retainer is shown in European Patent No. 37918, and another example is shown in British Patent Application No. 2 199 499. Another method of retaining a catheter on the body of a patient is shown in British published patent application number 2 211 417. Many other designs are known. However, none of the catheter retainers presently commercially available are entirely satisfactory. Surgeons therefore still quite frequently stitch a catheter to the skin of the wearer. This is frequently done when it is desired to drain a wound and yet hold the wound largely closed. This procedure of course involves a risk of infection and may be painful for the patient.

Prior art catheter retainers are unsatisfactory for a number of reasons. Firstly the retainer may be size dependent. In other words, for catheters of different diameter, a different catheter retainer device may be required. Another disadvantage is that known catheter retainers are often hard and rigid, and therefore uncomfortable to wear. Wearing them may promote lesions or maceration of the skin and so give rise to problems other than that for which the patient is in hospital. Another disadvantage of known catheter retainers is that they are hard to clean. Also, when used with catheters which are of a silicone rubber, a material commonly used for catheters, the catheter tubes are hard to lock in position relative to the retainer because of the slipperiness of the tube. As a result, patients can inadvertently pull catheters out. Yet another disadvantage of known catheter retainers is that the clamping pressure which most of them need to apply tends to collapse the catheter or the drainage tube. In consequence, the efficiency of drainage is adversely affected.

It would be desirable if there existed a catheter retainer which overcomes or at least greatly mitigates these disadvantages.

SUMMARY OF THE INVENTION

According to the invention, there is provided a catheter retainer comprising a pad of medical grade adhesive capable of attachment to the body of a person who has to use a catheter, in which the pad carries a member to which is secured a cotton or synthetic fibre thread, or a thread of like material, the thread being of such a length that it can be wound around the catheter at least once and preferably several times and also wound around the member.

It has been found that this arrangement gives a very simple yet effective catheter retainer.

According to a preferred embodiment of the invention, the member has a pair of ears or lugs which are upstanding from the non-adhesive surface thereof, and the thread is attached at one of its ends to one of these ears, the other ear having a slot in which the free end of the thread can be engaged after one or more turns around the catheter have been taken.

The invention as defined above has the great advantage of simplicity. The catheter retainer is easy to fix to the patient, and the winding of the thread around the catheter can be done with one hand if needed. Moreover, one catheter retainer can take two or more catheters. This is important and advantageous when it is necessary to have one catheter supplying liquid to the interior of the body and the other catheter dealing with drainage. A catheter retainer of this kind has an automatic safety feature in that if the catheter is inadvertently pulled, the thread tends to tighten and hence grip the catheter more tightly. The catheter is easily released by unwinding the thread.

In a modification of the invention, multiple tubing having parallel liquid paths can also be securely attached to the body of a patient.

Despite all the many attempts to design a satisfactory catheter retainer, the present invention is to the Applicant's best knowledge and belief, the first catheter retainer which relies upon a thread which is simply wound around the catheter. Either sufficient turns may be wound not to need anchoring of the free end or the thread after encircling the catheter may be anchored on another part of the catheter retainer device.

DESCRIPTION OF THE DRAWINGS

The invention will be better understood from the following illustrative description of one example, given with reference to the accompanying drawings, in which.

DESCRIPTION OF THE PREFERRED EMBODIMENTS

Figure 1:
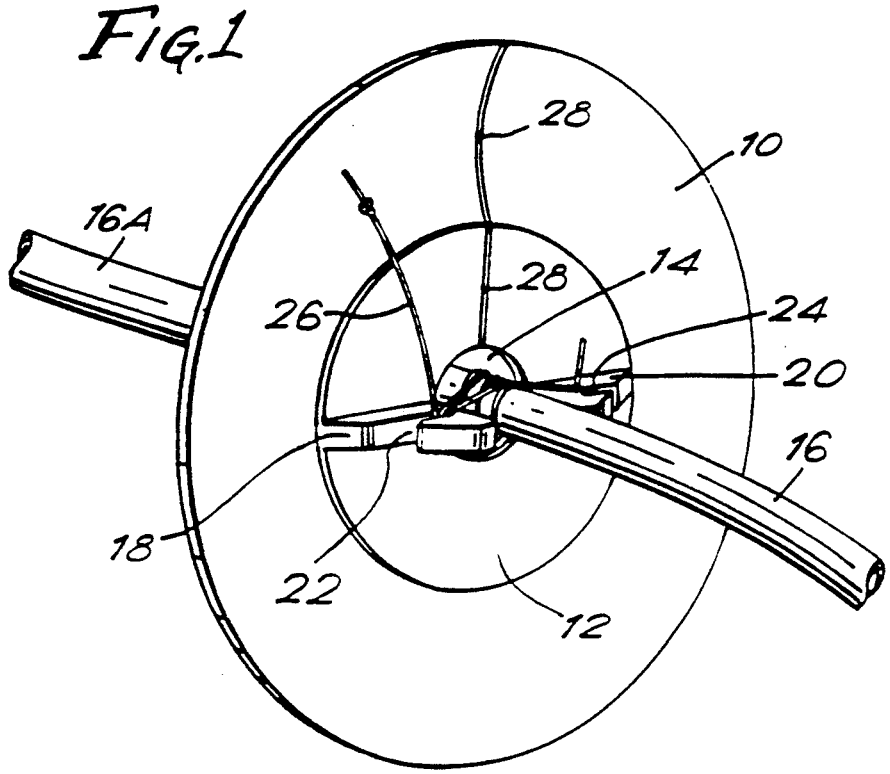
FIG. 1 is a perspective view of one example of catheter retainer according to the invention.

The catheter retainer illustrated in FIG. 1 of the drawings comprises a pad 10 of medical grade adhesive material, which as seen is a circular pad and which has a backing 12 of a synthetic plastics film. As seen, the pad 10 is circular and the film is concentric therewith but has a smaller diameter. The pad 10 may for example be of the medical grade adhesive known by the Trade Mark "STOMAHESIVE", available from ConvaTec Limited, of Hounslow, Middlesex, England. A central circular hole 14 extends through both pad and film. It is sized slightly larger than the outside diameter of a catheter 16 which is to be passed through it. In the drawing, the portion 16a of the catheter is that within the body of the wearer. The hole 14 could be of any shape.

Secured to the plastics film 12 are two members 18 and 20, each having respective slots 22, 24. A thread 26, for example about 100 mm (10 cms) in length, is attached to one of the members 20 and its free end, is, in use, wound around the catheter 16 a number of times and then slipped into the slot 22. The slot 22 may be tapered so that it becomes narrower towards its inner end. The thread is gripped firmly by this kind of slot.

When it is desired to release the catheter, the free end of the thread 26 is removed from the slot 22 and unwrapped, so releasing the catheter which can then be withdrawn, while the pad 10 remains on the body of the wearer.

Of course by having a larger central hole, more than one catheter can be similarly accommodated.

In a variation of the invention, a single member or post could be attached to the plastics film 12 and could act as the anchor point for the length of thread. In other words, one of the members 18 and 20 could be dispensed with.

Other variations are possible without departing from the invention. For example, the members 18 and 20 need not have the specific shape or form shown. So long as one anchor member is attached to the medical grade adhesive, serving for the attachment point for one end of the thread, then a catheter can be adequately retained by winding multiple turns of the thread around the catheter.

It is highly desirable, as shown, that the hole 14 should be connected by a cut or slit 28 to the exterior edge of the pad 10. In this way, the catheter can be put in place by passing it radially inwardly through this slot 28 rather than threading it through the hole 14 in a direction transverse to the plane of the pad 10.

Figure 2:
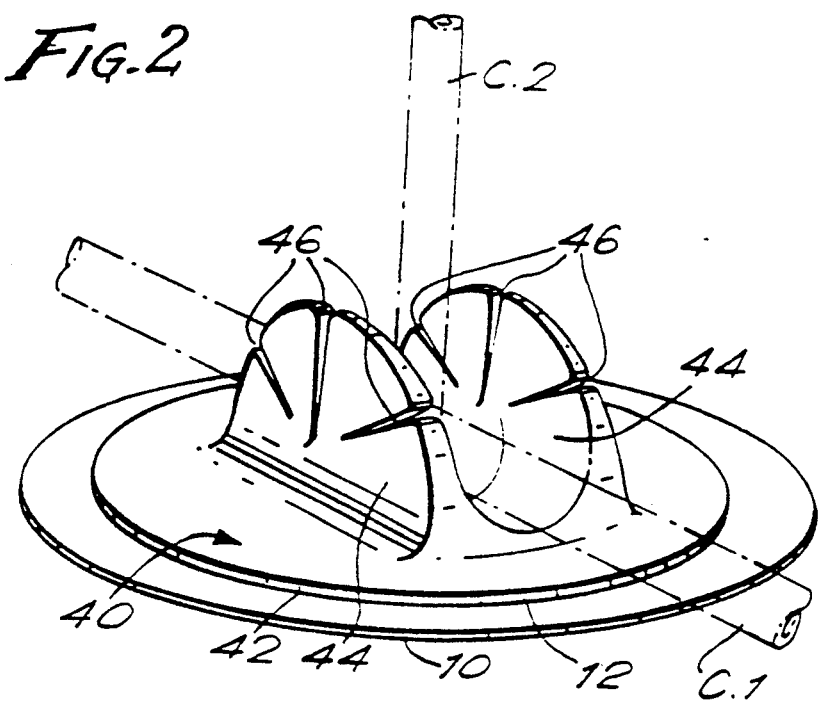
FIG. 2 is a perspective view of a second example of a catheter retainer according to the invention.

The catheter retainer illustrated in FIG. 2 also has a pad 10 of medical grade adhesive material which has a backing 12 of plastics film. Attached to the film is a thread attachment member 40 which may be of moulded plastics material. The member 40 has a disc or flange 42 which is attached (e.g. by adhesive) to the film 12. Two ears 44 are upstanding from the flange 42. Each of the ears is provided with three slots 46. These slots enable thread to be looped around in any desired manner so as to securely retain a catheter. Two possible positions for the catheter are shown at C.1 and C.2. The thread is not shown, for clarity, in FIG. 2.

I claim:

1. A catheter retainer comprising:
   a pad having a top surface and a bottom surface, said bottom surface having a medical grade adhesive thereon, said top surface having a pair of ears extending therefrom; and
   a thread attached at one of its ends to one of the ears, the other of said ears having a slot therein wherein the other end of said thread can be fixedly engaged, said thread being of a length so as to be capable of being wound around a catheter tube to be used with the retainer.

2. A catheter retainer according to claim 1 wherein each of said ears has at least one slot for receiving said thread.

3. A catheter retainer according to claim 1 wherein said pad includes a central aperture predeterminedly sized so as to accommodate a catheter tube extending therethrough.

4. A catheter retainer according to claim 3 wherein said central aperture is predeterminedly dimensioned to accommodate more than one catheter tube extending therethrough.

* * * * *